(12) United States Patent
Rothschild

(10) Patent No.: US 7,551,718 B2
(45) Date of Patent: Jun. 23, 2009

(54) SCATTER ATTENUATION TOMOGRAPHY

(75) Inventor: Peter J. Rothschild, Boston, MA (US)

(73) Assignee: American Science and Engineering, Inc., Billerica, MA (US)

(*) Notice: Subject to any disclaimer, the term of this patent is extended or adjusted under 35 U.S.C. 154(b) by 163 days.

(21) Appl. No.: 11/843,185

(22) Filed: Aug. 22, 2007

(65) Prior Publication Data
US 2008/0049899 A1    Feb. 28, 2008

Related U.S. Application Data

(60) Provisional application No. 60/823,328, filed on Aug. 23, 2006.

(51) Int. Cl.
*G01N 23/201* (2006.01)
(52) U.S. Cl. .......................... 378/88; 378/89
(58) Field of Classification Search ............ 378/86, 378/87, 88, 89
See application file for complete search history.

(56) References Cited

U.S. PATENT DOCUMENTS

| | | | |
|---|---|---|---|
| 2,670,401 A | 2/1954 | Weinberg | 178/6.8 |
| RE28,544 E | 9/1975 | Stein et al. | 250/369 |
| 3,955,089 A | 5/1976 | McIntyre | 250/399 |
| 4,002,917 A | 1/1977 | Mayo | 250/445 T |
| 4,144,457 A | 3/1979 | Albert | 250/445 |
| 4,149,076 A | 4/1979 | Albert | 250/402 |
| 4,194,123 A | 3/1980 | Wittry | 250/492 |
| 4,196,351 A | 4/1980 | Albert | 250/416 TV |
| 4,357,535 A | 11/1982 | Haas | 378/57 |
| 4,535,243 A | 8/1985 | Peschmann | 250/363 |
| 4,598,415 A | 7/1986 | Luccio et al. | 378/119 |
| 4,672,615 A | 6/1987 | Kelly et al. | 372/2 |
| 4,694,457 A | 9/1987 | Kelly et al. | 372/2 |
| 4,730,350 A | 3/1988 | Albert | 378/10 |
| 4,799,247 A | 1/1989 | Annis et al. | 378/87 |

(Continued)

FOREIGN PATENT DOCUMENTS

DE        26 39 631        3/1998

(Continued)

OTHER PUBLICATIONS

Harding, G., "*On the Sensitivity and Application Possibilities of a Novel Compton Scatter Imaging System*", IEEE Transactions on Nuclear Science, vol. NS-29, Nov. 3, Jun. 1982, pp. 1260-1265.

(Continued)

*Primary Examiner*—Chih-Cheng G Kao
(74) *Attorney, Agent, or Firm*—Bromberg & Sunstein LLP

(57) ABSTRACT

Methods for characterizing an inspected object on the basis of attenuation determined from pair-wise illuminated voxels. A beam of penetrating radiation characterized by a propagation direction and an energy distribution is scanned across an object, while scatter detectors with collimated fields-of-view detect radiation scattered by each voxel of the inspected object that is intercepted by the incident beam of penetrating radiation. By calculating the attenuation of penetrating radiation between pairs of voxels of incidence of the incident beam, a tomographic image is obtained characterizing the three-dimensional distribution of attenuation in the object of one or more energies of penetrating radiation, and thus of various material characteristics.

14 Claims, 7 Drawing Sheets

U.S. PATENT DOCUMENTS

| | | | |
|---|---|---|---|
| 4,864,142 A | 9/1989 | Gomberg | 250/390.04 |
| 4,868,856 A * | 9/1989 | Frith et al. | 378/86 |
| 4,884,289 A | 11/1989 | Glockmann et al. | 378/87 |
| 5,022,062 A | 6/1991 | Annis | 378/86 |
| 5,097,492 A | 3/1992 | Baker et al. | 378/22 |
| 5,153,900 A | 10/1992 | Nomikos et al. | 378/65 |
| 5,179,581 A | 1/1993 | Annis | 378/86 |
| 5,181,234 A | 1/1993 | Smith | 378/87 |
| 5,182,764 A | 1/1993 | Peschmann et al. | 378/57 |
| 5,247,561 A | 9/1993 | Kotowski | 378/87 |
| 5,260,982 A | 11/1993 | Fuji et al. | 378/87 |
| 5,313,511 A | 5/1994 | Annis et al. | 378/87 |
| 5,420,905 A | 5/1995 | Bertozzi | 378/88 |
| 5,430,787 A | 7/1995 | Norton | 378/87 |
| 5,442,678 A | 8/1995 | Dinsmore et al. | 378/137 |
| 5,504,796 A | 4/1996 | Da Silveria et al. | 378/121 |
| 5,548,630 A | 8/1996 | Hell et al. | 378/137 |
| 5,642,394 A | 6/1997 | Rothschild | 378/57 |
| 5,682,412 A | 10/1997 | Skillicorn et al. | 378/98.6 |
| 5,696,806 A | 12/1997 | Grodzins et al. | 378/86 |
| 5,712,889 A | 1/1998 | Lanzara et al. | 378/19 |
| 5,805,662 A | 9/1998 | Kurbatov et al. | 378/87 |
| 5,841,831 A | 11/1998 | Hell et al. | 378/19 |
| 5,930,326 A | 7/1999 | Rothschild et al. | 378/57 |
| 6,111,974 A | 8/2000 | Hiraoglu et al. | 378/4 |
| RE37,899 E | 11/2002 | Grodzins et al. | 378/86 |
| 7,203,276 B2 * | 4/2007 | Arsenault et al. | 378/87 |
| 2001/0046275 A1 | 11/2001 | Hussein | 378/7 |

FOREIGN PATENT DOCUMENTS

| | | |
|---|---|---|
| DE | 197 10 222 | 9/1998 |
| RU | 448413 | 11/1974 |

OTHER PUBLICATIONS

Murphy, E.E., "*A Rising War on Terrorists*", IEEE Spectrum, Nov. 1989, pp. 33-36.

Stein et al., "*Flying Spot X-Ray Imaging Systems*", American Science and Engineering, Inc., ASE-2864, Dec. 1971, pp. 1-17.

Stein et al., "*Flying Spot X-Ray Imaging Systems*", Materials Evaluation, American Society of Nondestructive Testing, vol. XXX, Nov. 7, Jul. 1972, pp. 137-148.

Stein, "*X-Ray Imaging with a Scanning Beam*", Radiology, vol. 117, Dec. 1975, pp. 713-716.

Towe et al., "*X-Ray Compton Scatter Imaging Using a High Speed Flying Spot X-Ray Tube*", IEEE Trans. Bromed. Eng. BME-28, Oct. 1981, pp. 717-721.

Tracy, E.J., "*A New X-Ray Scanner to Hinder Hijackers*", Fortune, Apr. 28, 1986, p. 146.

* cited by examiner

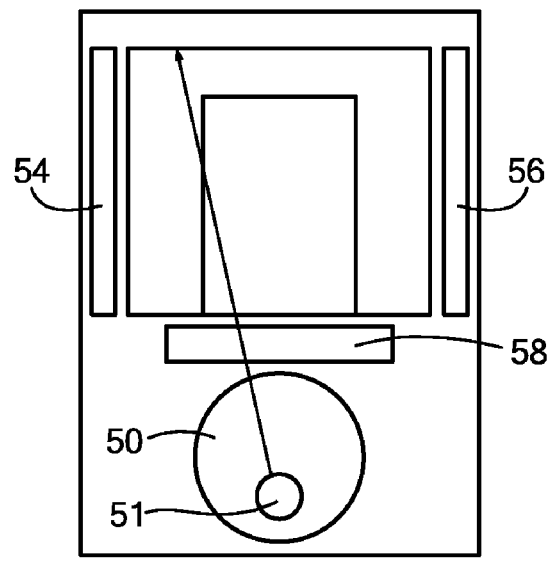
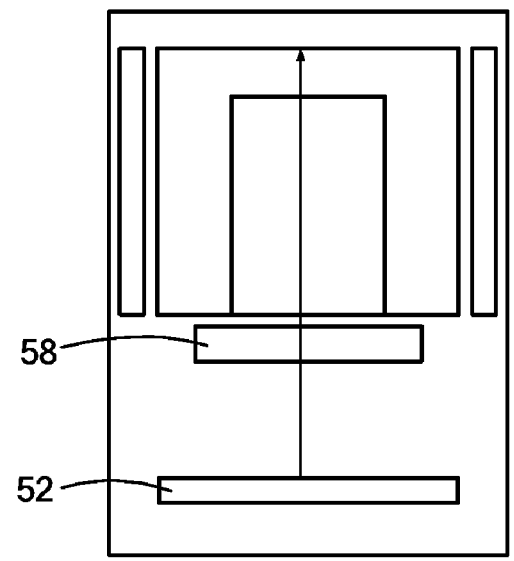
*FIG. 5A*  *FIG. 5B*
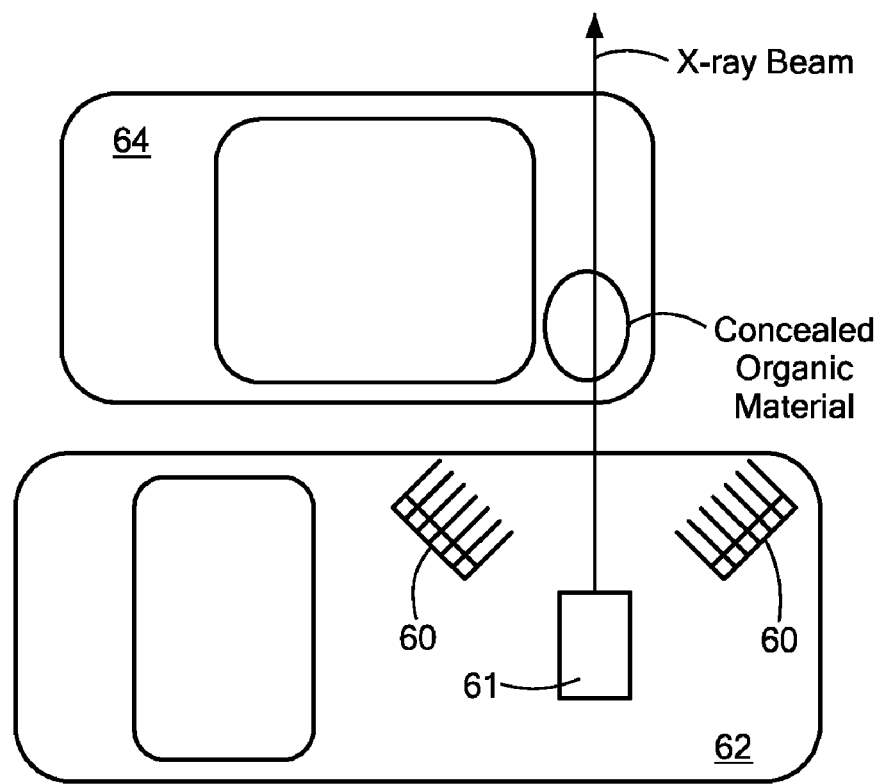
*FIG. 6*

SCATTER ATTENUATION TOMOGRAPHY

The present application claims priority from U.S. Provisional Patent Application, Ser. No. 60/823,328, filed Aug. 23, 2006, which application is incorporated herein by reference.

TECHNICAL FIELD

The present invention relates to methods and systems for inspecting objects by means of penetrating radiation, and more particularly, to inspection of objects by simultaneous detection of penetrating radiation scattered into distinct, and possibly opposing, directions.

BACKGROUND OF THE INVENTION

In the period since September, 2001, X-Ray Computerized Tomography (CT) has been used extensively to search for explosive materials concealed in airline baggage. The method works by measuring the "CT number" of objects contained in a suitcase. The CT number is essentially a measure of the attenuation per unit length of x-rays (with a given energy distribution) in the material comprising each object. The CT number can then be used to identify the material. As a matter of definition, "CT number," as used herein and in any appended claims, will refer to a measure of x-ray attenuation, conventionally quoted relative to the attenuation of water.

For organic materials, the CT number is essentially a measure of the electron density of the material, which in turn, is proportional to the mass density. X-Ray CT systems are therefore able to measure the mass density of concealed materials. Explosive materials tend to have mass densities which lie in the range of about 1.2-1.7 grams per cubic centimeter (g/cc). Since x-Ray CT systems reconstruct the contents of a container in three dimensions, the volume of each concealed object is also determined. Combining this information with the density yields the mass of each object. By selecting objects with a minimum size and mass which have a density between 1.2 and 1.7 g/cc, explosive threats can automatically be detected in the container, and an alarm sounded.

Disadvantages of x-Ray CT systems include their size and cost. Both the size and cost arise largely because of the rapidly rotating gantries on which the x-ray source and detector arrays are mounted.

U.S. Pat. No. 5,930,326, entitled "Side Scatter Tomography System," described a method for detecting radiation scattered at essentially 90 degrees out of a raster-scanning pencil beam of x-rays, as detected by one or more arrays of segmented and collimated detector arrays. The intensity distribution of the side-scattered radiation is then used to reconstruct (in three dimensions) the organic objects concealed within a container. That patent is incorporated herein by reference.

SUMMARY OF THE INVENTION

In accordance with preferred embodiments of the present invention, methods and a system are provided for characterizing an object on the basis of a determination of mean-free-path of penetrating radiation based upon pair-wise analysis of voxels. In various embodiments, the method entails:

generating an incident beam of penetrating radiation characterized by a propagation direction and an energy distribution;

disposing a plurality of detector elements about the beam of penetrating radiation each detector characterized by a field of view;

collimating the field of view of each detector element;

varying the propagation direction of the incident beam of penetrating radiation so as to be incident sequentially on the inspected object at a plurality of points of incidence;

detecting radiation scattered by voxels of the inspected object taken in pairs, the voxels defined as the intersection between a propagation direction of the incident beam and the field of view of a detector element;

calculating attenuation of penetrating radiation between pairs of voxels of incidence of the incident beam.

In accordance with further embodiments of the invention, step of detecting radiation may include detecting specified energy components of radiation scattered out of the incident beam of penetrating radiation. In addition to varying the propagation direction of the incident beam, the incident beam may be scanned in a pattern substantially transverse to the propagation direction so as to be incident on the inspected object at a plurality of points of incidence. The attenuation of penetrating radiation as a function of position within the inspected object may be displayed.

In accordance with other alternate embodiments of the invention, the step of disposing detectors about the incident beam of penetrating radiation may include disposing arrays of scatter detectors along directions having a vector component substantially parallel to the propagation direction of the incident beam, or may include disposing the detectors in a plane substantially transverse to the beam of penetrating radiation.

Calculating the attenuation of penetrating radiation may include determining a mean free path of scattered radiation as a function of position within the inspected object. Collimating may include restricting the field of view of each detector to a direction at a specified range of angles with respect to the propagation direction of the incident beam.

In accordance with yet further embodiments of the invention, the methods heretofore described may further include varying the energy distribution of the incident beam of penetrating radiation. Moreover, the step of scanning may include scanning an aperture with respect to an x-ray tube as well as activating discrete elements of a source array.

BRIEF DESCRIPTION OF THE DRAWINGS

The foregoing features of the invention will be more readily understood by reference to the following detailed description taken with the accompanying drawings:

FIGS. 5A and 5B depict systems scanning baggage and small parcels in accordance with embodiments of the invention;

FIG. 6 depicts a system in which the scatter detectors are disposed to one side of the inspected object, as in a mobile inspection unit;

DETAILED DESCRIPTION OF THE EMBODIMENT OF THE INVENTION

The current invention builds upon the teachings of U.S. Pat. No. 5,930,326 by describing a simple and elegant method for determining a much more accurate measurement of the density of concealed organic objects. In accordance with preferred embodiments of the present invention, the sidescatter distribution is detected in two detector arrays. The method allows for a full three-dimensional reconstruction of the organic contents of the container, along with the more accurate density determination that could be obtained using the methods taught in U.S. Pat. No. 5,930,326.

As now described with reference to FIG. 1, Scatter Attenuation Tomography, generally, looks at the fall-off, in the sidescattered radiation, from a raster-scanning x-ray beam as the beam moves deeper into an object of interest.

It is to be noted that while the present description refers to an incident beam 10 of penetrating radiation as an x-ray beam, it is to be understood that any beam of penetrating radiation falls within the ambit of the present invention. Thus, the beam may include x-rays, or gamma rays, etc.

Figure 1:
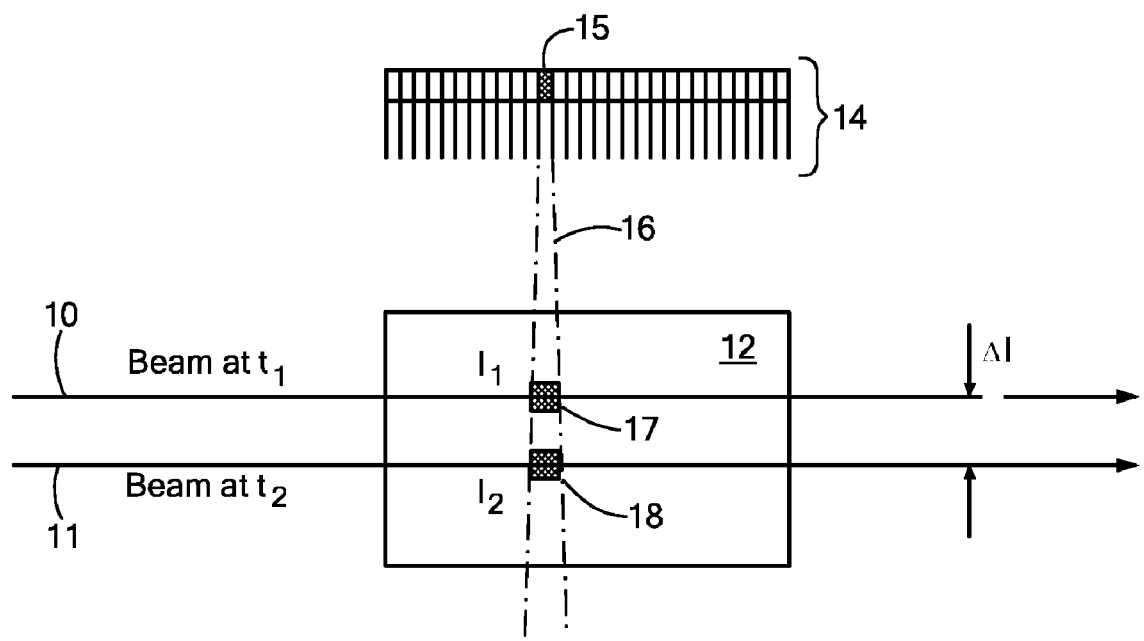
FIG. 1 depicts the principle of operation of a Scatter Attenuation Tomography system in accordance with embodiments of the present invention.

In FIG. 1, the raster scanning x-ray beam 10 comes in from the left and passes through a block 12 of organic material. At times $t_1$ and $t_2$, x-ray beam 10 is characterized by intensity $I_1$ and $I_2$, respectively, and instantaneous positions are a designated by numerals 10 and 11 in FIG. 1. A segmented scatter detector array 14 is located above the organic material, and each detector element 15 in array 14 is collimated such that its field of view 16 for detecting scattered radiation is directly below it, or, equivalently, such that its field of view is perpendicular to the propagation direction of the incident beam 10. One of the detector elements 15 is highlighted, and at times $t_1$ and $t_2$ it detects scattered radiation emitted from volume elements 17 and 18, respectively, contained within organic material 12. The ratio of the strengths $S_1$ and $S_2$ of the scattered radiation detected in the $i^{th}$ detector element at times $t_1$ and $t_2$ is given by:

$$S_2/S_1 = (I_2/I_1) \cdot A(\Lambda), \qquad \text{Eqn. 1}$$

where $A(\Lambda)$ is an attenuation factor characterizing the scattered radiation in the organic material over the distance $\Delta 1$ separating the two beams, and $\Lambda$ is the mean free path of the scattered radiation in the organic material. The attenuation factor $A(\Lambda)$ is given by:

$$A(\Lambda) = e^{-\Delta 1/\Lambda}. \qquad \text{Eqn. 2}$$

It can be seen that, for the simple geometry shown in FIG. 1, the intensity of the incident x-ray beam at the two voxels is equal ($I_1 = I_2$). In this case, Eqn. 1 yields $$A(\Lambda) = S_2/S_1, \qquad \text{Eqn. 3}$$

and therefore the attenuation (and hence the mean free path $\Lambda$ of the radiation in the organic material) can simply be determined from the ratio $S_2/S_1$. Since the mean free path for organic materials is essentially proportional to the mass density, the density of the material can be inferred.

In realistic cases, however, the beam intensities $I_1$ and $I_2$ will not, in general, be equal. This could happen, for example, if organic material 12 were rotated with respect to the beams 10 and 11, or if an intervening object 20 block one of the incident beams as shown in FIG. 2.

Figure 2:
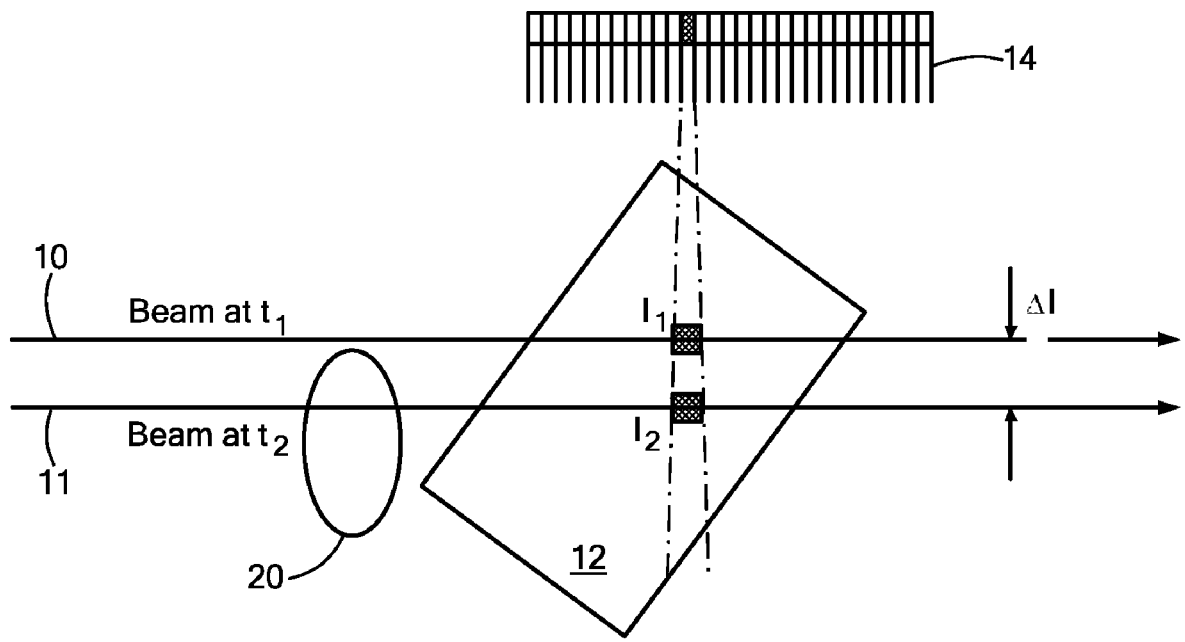
FIG. 2 depicts a geometry in which an intervening object is interposed within one of the incident beams in the system of FIG. 1.

In the case depicted in FIG. 2, since $I_1 \neq I_2$, Eqn. 1 indicates that $A(\Lambda) \neq S_2/S_1$. In fact, since $I_1$ and $I_2$ are not known, the attenuation can not be determined from Eqn. 1.

Figure 3:
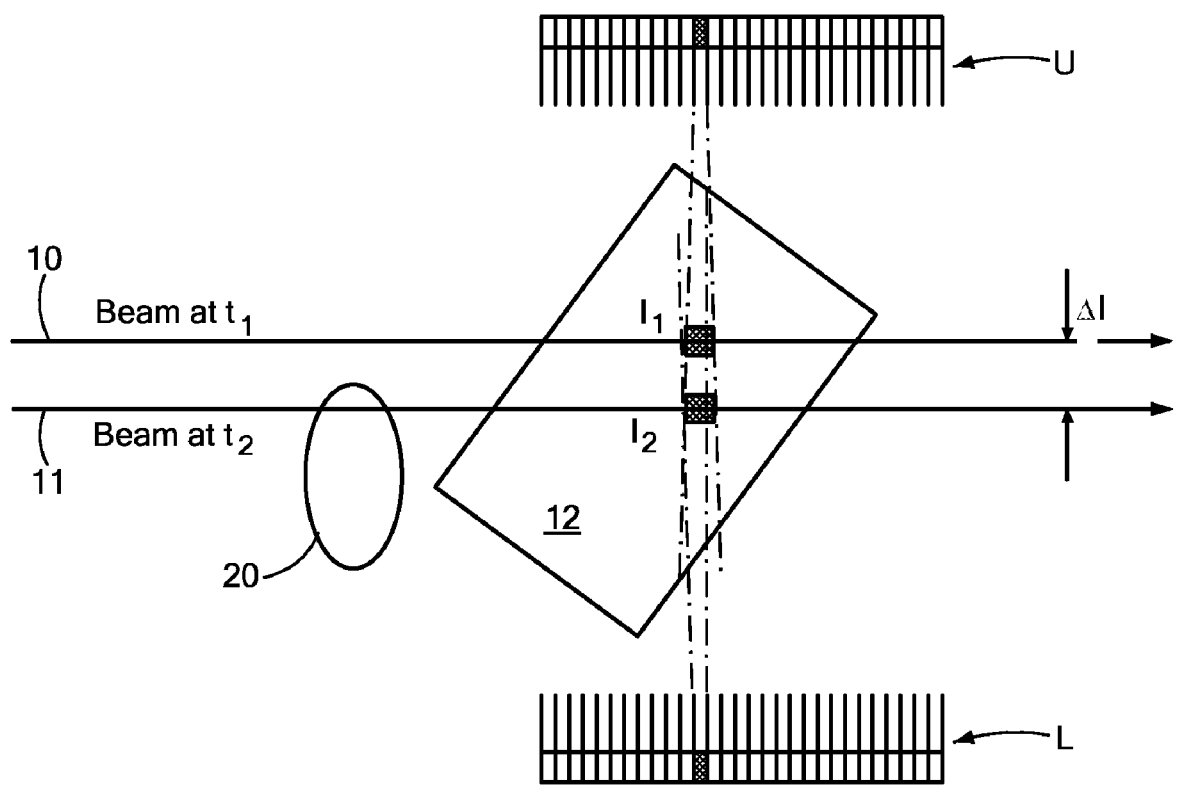
FIG. 3 is a schematic depiction of a preferred embodiment of the present invention in which detector elements of opposing detector arrays detect penetrating radiation sidescattered by an inspected object.

The current invention provides heretofore unavailable solutions to this problem, as now described with reference to FIG. 3. In accordance with preferred embodiments of the present invention, two sidescatter arrays are provided, an upper sidescatter array U and a lower sidescatter array L. It is to be understood, of course, that the reference to upper and lower directions is arbitrary, and arrays of detectors may be disposed in directions that have a vector component substantially parallel to the propagation direction of the incident beam of penetrating radiation are within the scope of the present invention. Thus, the upper and lower detector arrays U and L shown in FIG. 3 may also be labeled left and right arrays, for example.

The ratio of the scatter intensities in the highlighted detector element of the upper detector array at times $t_1$ and $t_2$ is given by:

$$U_2/U_1 = (I_2/I_1) \cdot A(\Lambda). \qquad \text{Eqn. 4}$$

Similarly, the ratio of signals in the lower detector array is given by:

$$L_1/L_2 = (I_1/I_2) \cdot A(\Lambda). \qquad \text{Eqn. 5}$$

Multiplying equations 4 and 5 together yields:

$$A(\Lambda) = \sqrt{[L_1 U_2/(L_2 U_1)]}. \qquad \text{Eqn. 6}$$

It can be seen that the expression for the attenuation factor in Eqn. 6 is now completely independent of the unknown beam intensities $I_1$ and $I_2$, and is independent of how the organic material 12 is oriented in the bag, or the number of surrounding objects 20 which may be occluding the incident beams. The only requirement is that there exist sufficient intensity in the two incident beams and a sufficiently clear path for the scattered radiation to reach each of the two detector arrays.

Figure 4:
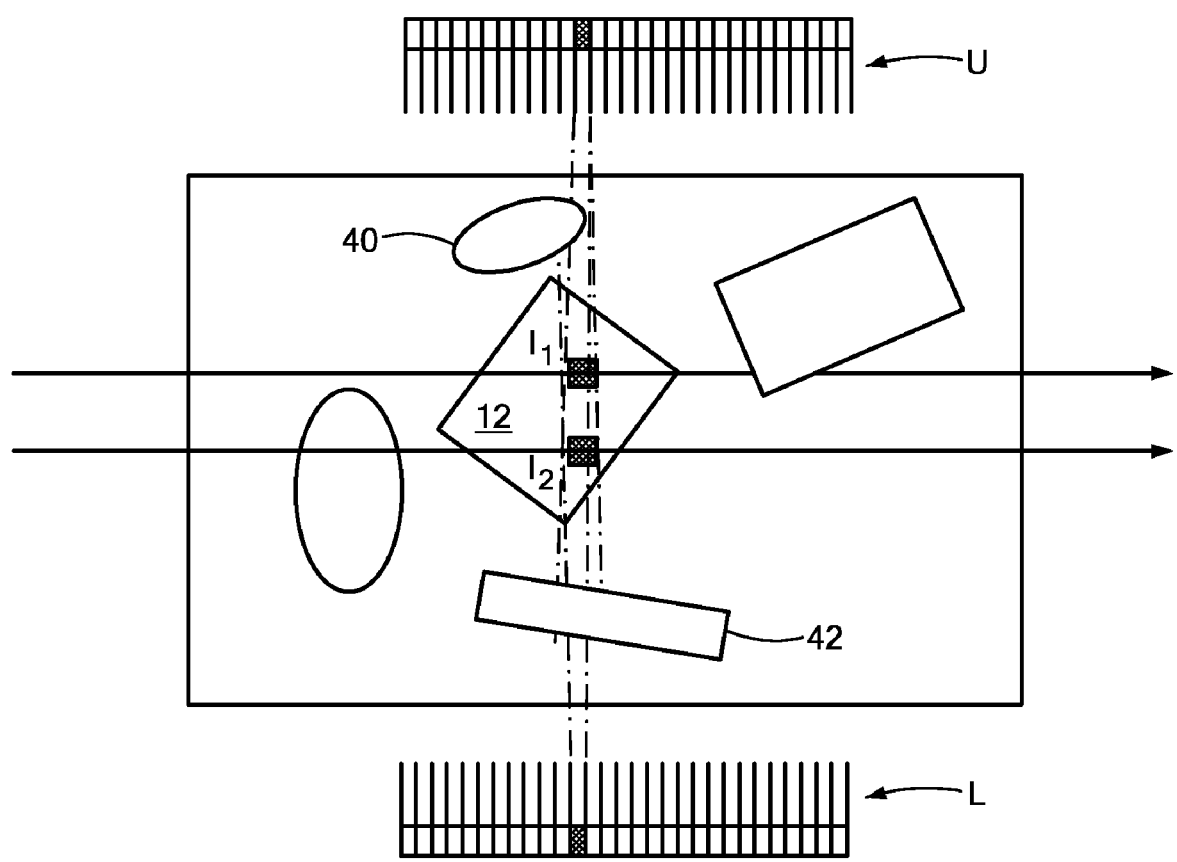
FIG. 4 schematically depicts a scenario in which two surrounding objects are located between an object under inspection and the upper and lower scatter array elements.

Another powerful aspect of the invention is that since only ratios of the scatter intensities are used (for example, only the ratios $L_1/L_2$ and $U_2/U_1$ appear in Eqn. 6), the method for calculating the attenuation factor given by Eqn. 6 is immune to any surrounding objects 20 which may attenuate the scattered radiation before it reaches one or both of the detector arrays. This is shown schematically in FIG. 4, where two surrounding objects 40 and 42 are now located between the organic material 12 under inspection and the upper U and lower L scatter arrays. In this scenario, the attenuation in organic block 12 (and hence its density) can still be determined, despite the surrounding "clutter" occluding both the incident beams and the scattered radiation.

Additional Corrections to the Scatter Data

Equations 4 and 5 are based on the assumption that the voxels on beams 1 and 2 from which the scatter is originating are essentially the same distance from each of the detector arrays. In actual fact, the voxel on beam 1, in the general case, will be at a different distance from each of the detector arrays than the voxel on beam 2. In order to correct for these differences, equations 4 and 5 become:

$$U_2/U_1 = (I_2/I_1) \cdot (d\Omega_{U2}/d\Omega_{U1}) \cdot A(\Lambda) \quad \text{Eqn. 7}$$

$$L_1/L_2 = (I_1/I_2) \cdot (d\Omega_{L1}/d\Omega_{L2}) \cdot A(\Lambda) \quad \text{Eqn. 8}$$

where, for example, $d\Omega_{L1}$ is the solid angle of the detector element in the lower array for the voxel located on beam 1. With these solid angle corrections, Eqn. 6 now becomes:

$$A(\Lambda) = \sqrt{[L_1 U_2/(L_2 U_1) \cdot d\Omega_{L2} d\Omega_{U1}/(\Omega d_{L1} d\Omega_{U2})]} \quad \text{Eqn. 9}$$

In general, the effect of the solid angle correction factor $d\Omega_{L2} d\Omega_{U1}/(d\Omega_{L1} d\Omega_{U2})$ is fairly small, and typically has a value close to unity.

Exemplary Embodiments of the Invention

The measurement of the attenuation (and therefore the density) of concealed organic materials implied by Eqn. 9 can be implemented in any system that uses a pencil beam of x-rays and which contains two segmented arrays of scatter detectors. Two systems for scanning baggage and small parcels are shown in FIGS. 5A and 5B wherein the source of penetration radiation is comprised, respectively, of a hoop with a scanning aperture about an x-ray tube 51, and a carbon nano-tube x-ray source array 52, comprised of discrete elements that may be addressably activated, as described, for example, in co-pending U.S. patent application Ser. No. 11/737,317, filed Apr. 19, 2007, and incorporated herein by reference. In either case, a left detector array 54 and a right detector array 56 are provided, for application as described above. Additionally, a backscatter array 58 may be disposed between the source and the inspected object so as to provide additional imaging or material characterization information.

Alternatively, the method of the invention may also be used to inspect concealed materials inside a container, where access to the sides of the container (for positioning the detector arrays) is not practical. Such a scheme is shown in FIG. 6, where angled, collimated detector arrays 60 are located in the backward direction, toward x-ray source 61. In the embodiment depicted in FIG. 6 by way of example, x-ray source 61 and detector arrays 60 are mounted in a mobile x-ray backscatter imaging system, on platform 62, for example, that is being used to inspect vehicles 64.

Figure 7:
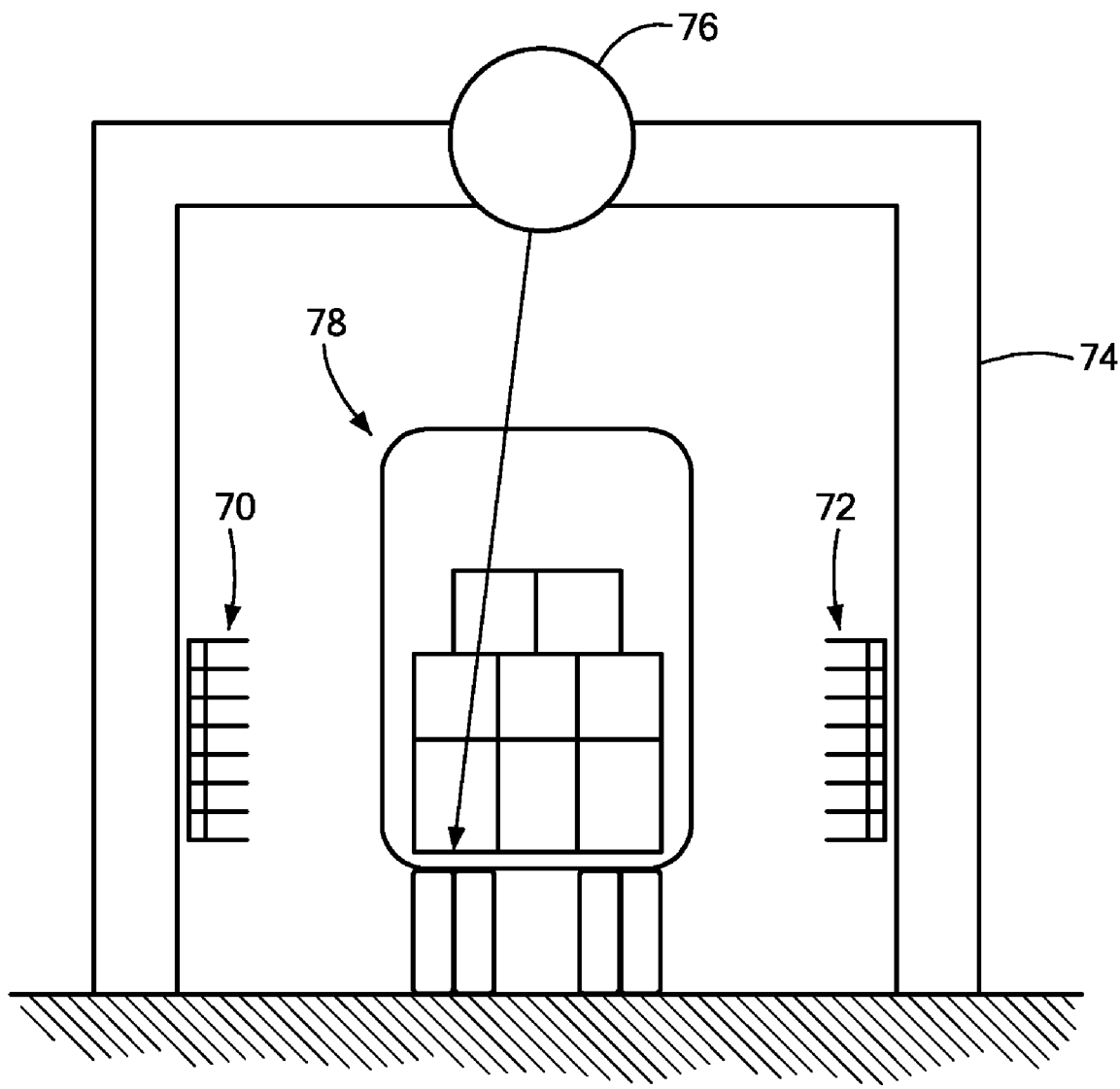
FIG. 7 shows an embodiment of the invention in which the source is disposed above the inspected object, and scatter detector arrays are disposed to either side.

In FIG. 7, an alternative embodiment that scans vehicles or other containers from above is shown. In this case the detectors 70 and 72 are mounted on the sides of the system (which could, for example, be based on a portal 74 or a gantry), while x-ray source 76 is disposed above the inspected object 78.

Figure 8B:
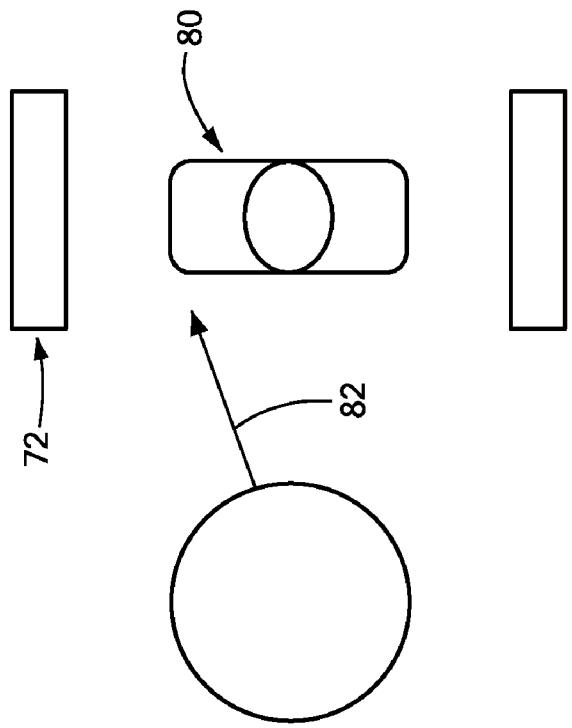
FIGS. 8A and 8B show embodiments of the present invention for inspection of personnel in which the source of penetrating radiation is disposed, respectively, above (or below), and in a horizontal plane with respect to, an inspected subject.
Figure 8A:
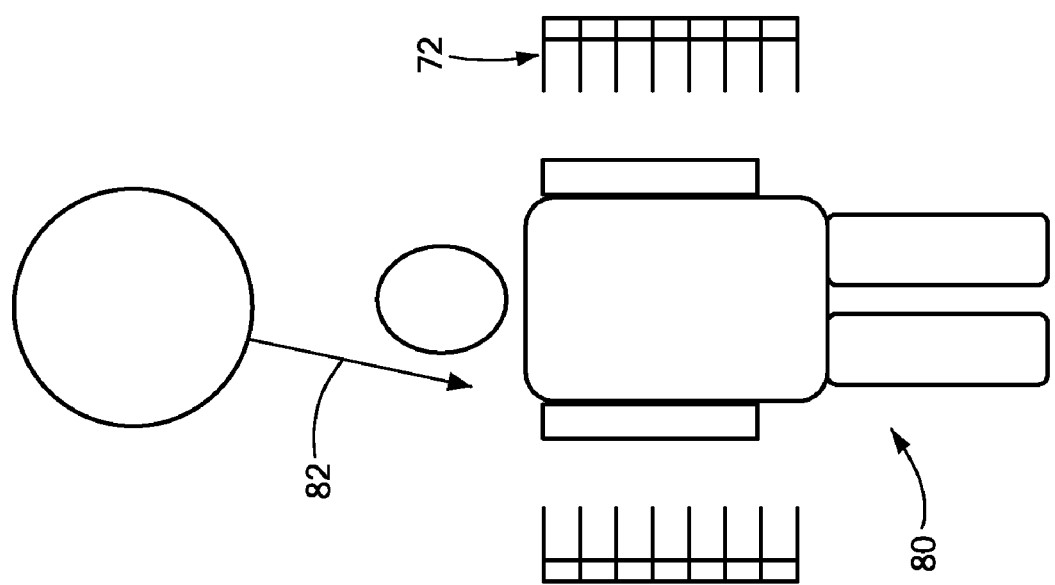

In FIGS. 8A and 8B, two alternate embodiments for detecting contraband organic materials carried by people in bags or backpacks, or concealed under clothing are shown. In FIG. 8A, an embodiment is shown wherein a person 80 is scanned by an x-ray beam 82 incident from above. X-ray beam 82 may also be positioned to scan the person from below. FIG. 8B shows an embodiment, depicted schematically from above, where the person 80 is scanned by an x-ray beam 82 which remains essentially in the horizontal plane. In each case, the detector arrays 72 are positioned on either side of the person 80.

Figure 9:
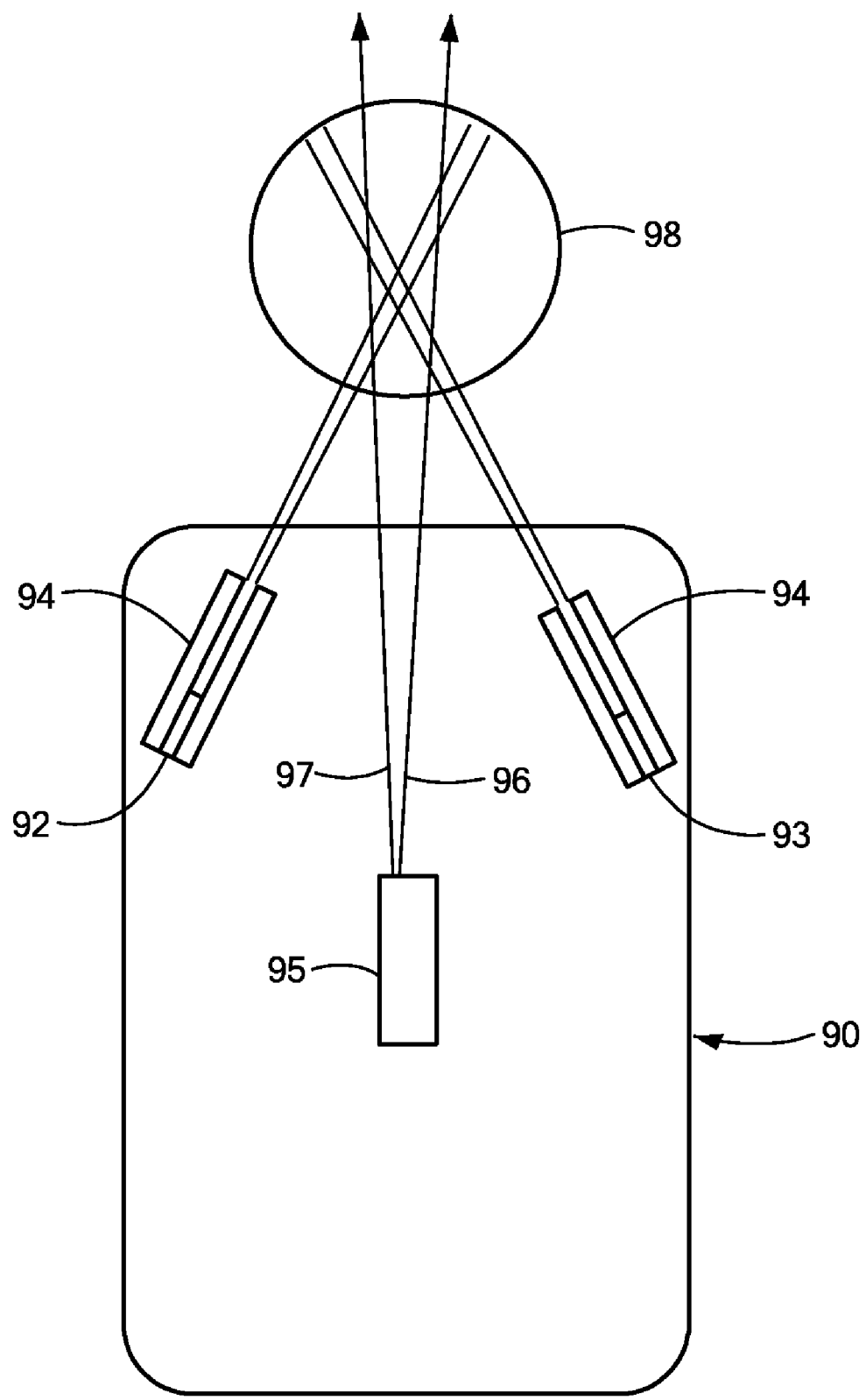
FIG. 9 shows a hand-held inspection device containing two collimated x-ray detectors, and a source emitting a plurality of scanned x-ray beams, in accordance with an embodiment of the present invention.

An alternate embodiment of the invention, which may be used as a hand-held device, is shown in FIG. 9. In this embodiment, a device 90 contains two single collimated x-ray detector units 94, each containing a detector 92 and 93. Additionally, device 90 contains a source 95 emitting a plurality of scanned x-ray beams 96 and 97, as described above, or alternatively, it may emit two fixed beams as shown, with only one being active at any given time. Beams 96 and 97 may be activated, sequentially, by use of shutters, for example. The emitted beams alternate in time, allowing for the attenuation factor of concealed organic materials 98 to be determined in accordance with Eqn. 6.

Dual Energy Embodiment of the Invention

The expression for the attenuation factor given in Eqn. 6, $$A(1) = \sqrt{[L_1 U_2/(L_2 U_1)]},$$

enables the mean free path $\Lambda$ of the scattered radiation to be measured for a particular piece of concealed organic material. By varying the energy of the raster-scanning pencil beam, the mean free path $\Lambda$ of the material can be measured for several different energy ranges of x-rays. By analyzing how the mean free path $\Lambda$ of the material changes with x-ray energy, a determination of the approximate effective atomic number Z of the material can be inferred, in addition to the measurement of the material density. For example, the mean free path for higher Z materials will decrease more rapidly with decreasing photon energy, compared with lower Z materials. This is due to the strong dependence of the photoelectric effect (which absorbs x-rays) on the effective atomic number of the material. The photoelectric absorption cross section increases rapidly with the effective atomic number of the material with decreasing x-ray photon energy.

Alternatively, rather than varying the energy of the raster-scanning x-ray beam, energy-sensitive detector elements can be used in the detector arrays. One such example of this includes the use of CdZnTe detectors, which enable the energy of each detected x-ray to be measured. Cuts can then be made on the energies of the detected x-rays, and the attenuation factor given by Eqn. 6 can then be calculated for several different ranges of x-ray energies. This then allows the mean free path of the material to be calculated for several different average x-ray energies, allowing both density and effective atomic number measurements of the material to be made. Having both these measurements allows for a more accurate identification of the material making up the organic object, increasing detection rates and lowering false alarm rates. Note that each of the alternate embodiments of the invention described previously can be extended to include dual-energy operation.

In accordance with certain further embodiments of the invention, material may be identified as a threat substance based on a comparison of a mean free path, calculated in accordance with the foregoing teachings, with a table of measured values. A calculated attenuation may be validated by repeat interrogation of a voxel with detector elements of opposing field of view.

All of the heretofore described embodiments of the invention are intended to be merely exemplary and numerous variations and modifications will be apparent to those skilled in the art. All such variations and modifications are intended to be within the scope of the present invention as defined in any appended claims.

What is claimed is:

1. A method for characterizing an object on the basis of mean-free-path of penetrating radiation, the method comprising:
   generating an incident beam of penetrating radiation, the incident beam characterized by a propagation direction and an energy distribution;
   disposing a plurality of detector elements about the beam of penetrating radiation, each detector element characterized by a field of view;
   collimating the field of view of each detector element;

detecting radiation scattered from a plurality of voxels lying within the inspected object, each voxel being defined as the intersection of the field of view of one of the detector elements and the propagation direction of the incident beam of penetrating radiation;

calculating attenuation of scattered penetrating radiation between pairs of voxels, each voxel of the pair corresponding to one of at least two propagation directions of the incident beam of penetrating radiation; and characterizing the object on the basis of the calculation and the mean-free-path of penetrating radiation.

2. A method in accordance with claim 1, further comprising varying the propagation direction of the incident beam of penetrating radiation so as to be incident sequentially on the inspected object at a plurality of points of incidence.

3. A method in accordance with claim 1, wherein the step of detecting radiation includes detecting specified energy components of the radiation scattered out of the incident beam of penetrating radiation.

4. A method in accordance with claim 1, further comprising:

scanning the incident beam in a pattern substantially transverse to the propagation direction so as to be incident on the inspected object at a plurality of points of incidence.

5. A method in accordance with claim 1, further comprising a step of displaying the attenuation of penetrating radiation as a function of position within the inspected object.

6. A method in accordance with claim 1, wherein the step of disposing detector elements about the incident beam of penetrating radiation includes disposing arrays of scatter detector elements along directions having a vector component substantially parallel to the propagation direction of the incident beam.

7. A method in accordance with claim 1, wherein the step of disposing detector elements about the incident beam of penetrating radiation includes disposing detector elements in a plane substantially transverse to the beam of penetrating radiation.

8. A method in accordance with claim 1, wherein calculating the attenuation of penetrating radiation includes determining a mean free path of scattered radiation as a function of position within the inspected object.

9. A method in accordance with claim 1, wherein the step of collimating includes restricting the field of view of each detector element to a direction at a specified range of angles with respect to the propagation direction of the incident beam.

10. A method in accordance with claim 1, further comprising varying the energy distribution of the incident beam of penetrating radiation.

11. A method in accordance with claim 1, wherein the step of scanning includes scanning an aperture with respect to an x-ray tube.

12. A method in accordance with claim 1, wherein the step of scanning includes activating discrete elements of a source array.

13. A method in accordance with claim 1, further comprising identifying a material as a threat substance based on a comparison of a calculated mean free path with a table of measured values.

14. A method in accordance with claim 1, further comprising validating a calculated attenuation based on a repeat interrogation of a voxel with detector elements of opposing field of view.

* * * * *